United States Patent [19]

Johnson et al.

[11] Patent Number: 4,608,439

[45] Date of Patent: Aug. 26, 1986

[54] PROCESS FOR PREPARING SUBSTITUTED ANTHRA[1,9-CD]PYRAZOL-6(2H)-ONES

[75] Inventors: Judith L. Johnson, Ypsilanti; Hollis D. Showalter, Ann Arbor, both of Mich.

[73] Assignee: Warner-Lambert Company, Morris Plains, N.J.

[21] Appl. No.: 727,637

[22] Filed: Apr. 26, 1985

[51] Int. Cl.$^4$ .................................. C07D 231/54
[52] U.S. Cl. .................................... 548/357
[58] Field of Search .......................... 548/357

[56]  References Cited

U.S. PATENT DOCUMENTS 4,556,654  12/1985  Showalter et al. .............. 548/357

OTHER PUBLICATIONS

Freifelder, J. Am. Chem. Soc., 82, pp. 2386–2389 (1960).

Primary Examiner—Richard A. Schwartz
Assistant Examiner—Kurt G. Briscoe
Attorney, Agent, or Firm—Elizabeth M. Anderson

[57]  ABSTRACT

An improved process for making anthra[1,9-cd]pyrazol-6(2H)-ones from 1,4-dichloro-5,8-disubstituted-9,10-anthracenediones and a hydrazine is disclosed. The compounds produced have antibacterial, antifungal, antileukaemic, and antitumor activity.

11 Claims, No Drawings

PROCESS FOR PREPARING SUBSTITUTED ANTHRA[1,9-CD]PYRAZOL-6(2H)-ONES

BACKGROUND OF THE INVENTION

The compounds of the present invention have been described in U.S. application Ser. No. 507,961 filed June 28, 1983 now U.S. Pat. No. 4,556,654.

The compounds were prepared by reacting a compound having the structural formula

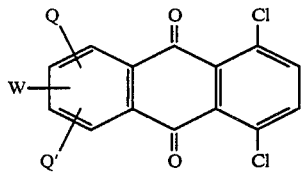

with a hydrazine of the general formula $H_2N\text{-}NHZ$, wherein Q, Q', and W may be the same or different and are H, OH, alkoxy of one to four carbon atoms, chlorine, benzyloxy, p-chlorobenzyloxy, and p-methoxybenzyloxy, Z is that portion of a hydrazine of formula DNHR' wherein D is a straight or branched alkylene of from two to eight carbon atoms and R' is an alkyl of from two to eight carbon atoms which may be substituted with an OH to produce a compound of structural formula

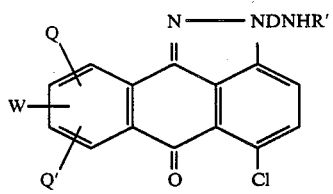

The crude product of this reaction was purified with difficulty by chromatography. The compound of Formula II was then treated directly with diamine of formula

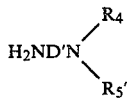

wherein $R_4$ is H or an alkyl of from one to eight carbon atoms and $R_5'$ is benzyl or H to produce a compound of the structural formula

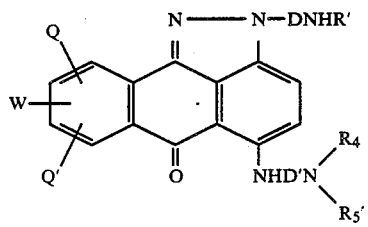

wherein D' is a straight or branched alkylene of from two to eight carbon atoms.

Alternatively, the crude product II was treated with diamine of formula

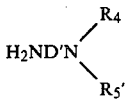

wherein $R_4$ is H or an alkyl of from one to eight carbon atoms and $R_5'$ is benzyl to produce compound of the structural formula which was purified by chromatography.

This compound may then be debenzylated by a standard procedure to produce the corresponding compound having structural formula

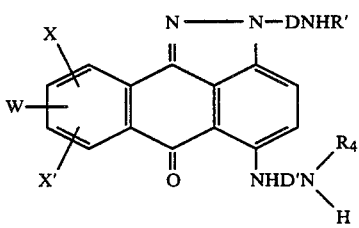

wherein X and X' may be the same or different and are H or OH.

The compounds are useful as antibacterial and antifugal agents.

Certain of the compounds in the invention display in vivo antileukemic activity. Certain of the compounds display in vitro activity against solid tumors.

SUMMARY OF THE INVENTION

The present invention relates to an improved process for the preparation of substituted anthra[1,9-cd]pyrazol-6(2H)-ones. While the yields approximate those of the prior invention, this improved synthesis does not require the time-consuming chromatography separation procedure used in the prior invention.

The synthesis is for compounds having the structural formula

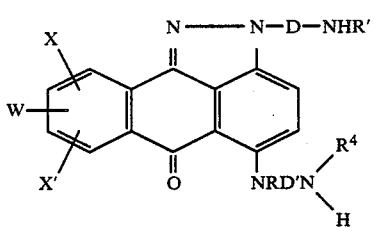

wherein X, X', and W may be the same or different and are H or OH; R is H or alkyl of from one to six carbon atoms; D and D' may be the same or different and are straight or branched alkylene groups of from two to eight carbon atoms; $R_4$ is H or an alkyl group of from one to eight carbon atoms; and R' is an alkyl group of from two to eight carbon atoms which may be substituted with OH.

The process proceeds as follows:
Compounds of structural formula

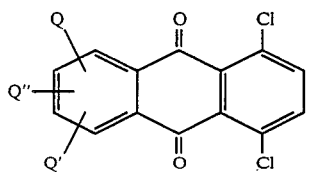

are reacted with a hydrazine of formula

H₂NNHDNHR' wherein Q, Q', and Q" may be the same or different and are H, benzloxy, p-chlorobenzyloxy, and p-methoxybenzyloxy, and D and R' are as defined above to produce a compound of structural formula

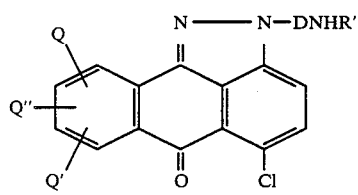

Compounds of structural Formula VII are reacted with a benzyl halide in a suitable solvent to give compounds of structural formula

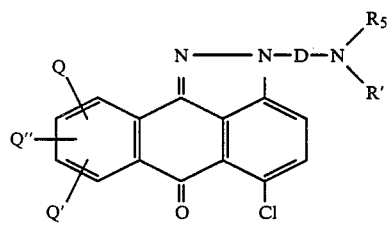

wherein R₅ is benzyl.

Compounds of VIII are reacted with a diamine of the formula

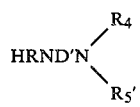

to produce compounds of structural formula

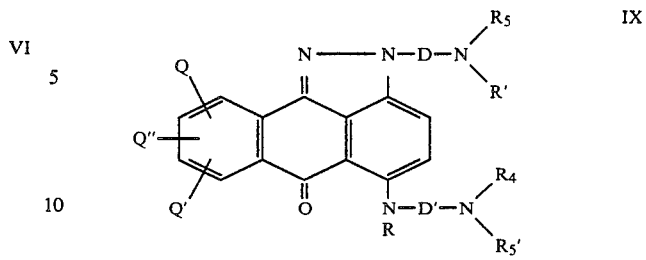

which are debenzylated by a standard procedure to produce compounds of the structural Formula V in summary.

DETAILED DESCRIPTION OF THE INVENTION

A process for the preparation of a substituted anthra[1,9-cd]pyrazol-6(2H)-one having the structural formula

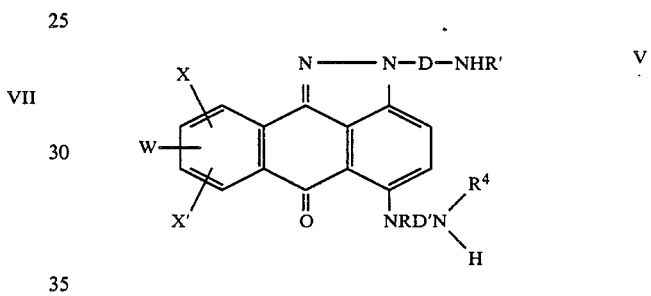

wherein X, W, X', D, R', D', and R₄ are defined hereinabove, from a compound having the structural formula

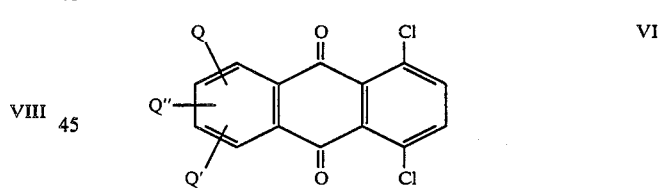

has been disclosed in U.S. application Ser. No. 507,961 filed June 28, 1983 now U.S. Pat. No. 4,556,654. That process includes chromatographic separation and recrystallization procedures which are very time-consuming. In the instant invention the chromatographic step is not required. Crystallization is carried out only once at the end of the reaction sequence to purify the final product.

For purposes of illustration the following schematic diagram shows alternate preparation procedures. Steps A, B, and C are illustrated in the prior art. Steps A, F, G, and H illustrate the process for the present invention to prepare the same compound.

Steps A, D, and E illustrate the prior art. Steps A, F, J, and K are illustrative of the process of the present invention for preparing the same compound.

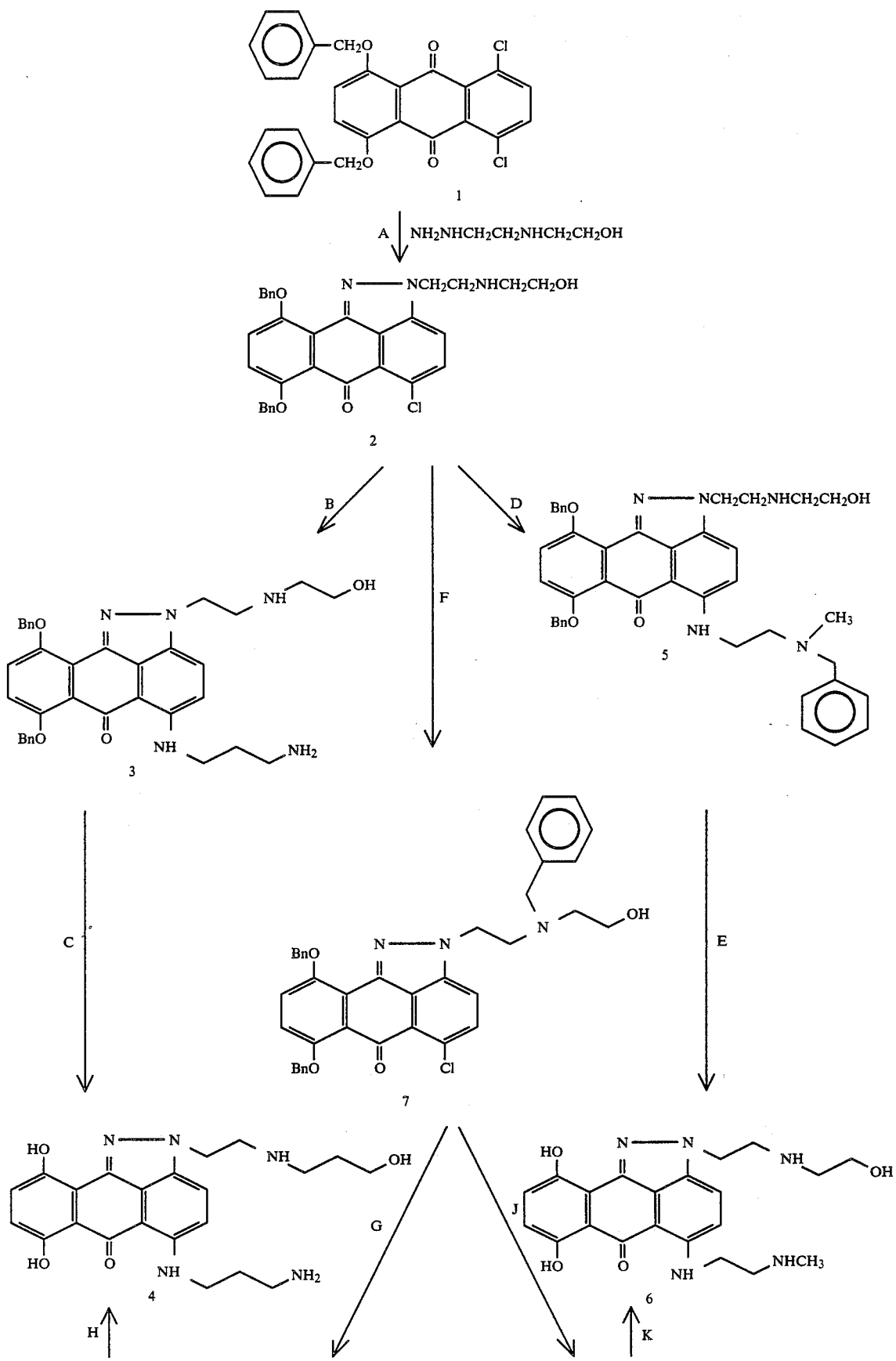

-continued

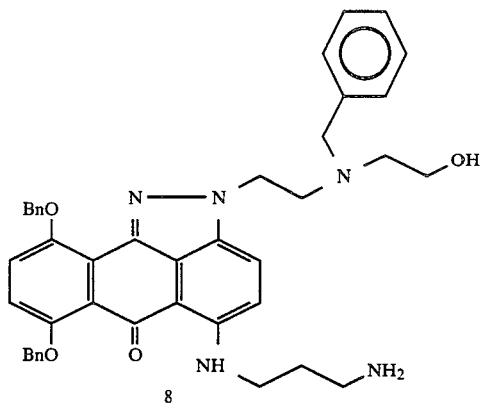
8

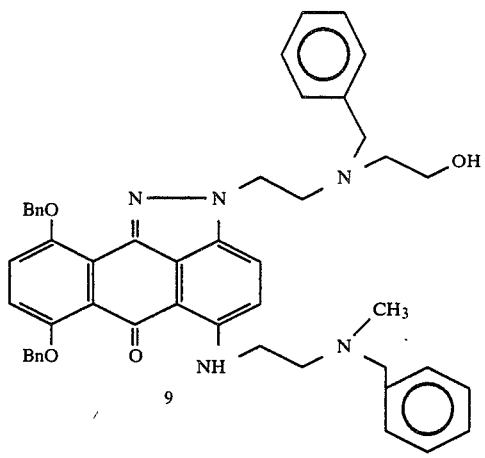
9

The reaction step "A" involves the reaction of a compound of the structural formula VI

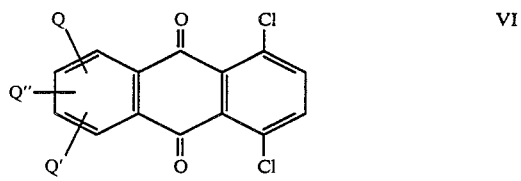

with a hydrazine of formula H₂NNHDNHR' wherein Q, Q', Q", D, and R' are defined hereinabove. The reaction may be accomplished in a variety of inert solvents by mixing a compound of structural Formula VI with a hydrazine in a 1:3 molar ratio. Use of a catalyst such as potassium fluoride and potassium bicarbonate may improve a particular yield. Dimethylacetamide or dimethysulfoxide is the preferred solvent. Suitable reaction temperatures are from 30°-85° C. The reaction is allowed to proceed for from 6 to 24 hours. It is generally observed that increasing the reaction temperature will decrease the time necessary for completing the reaction. The proper choice of reaction variable is within the skill of the art. At the completion of the reaction the product is isolated by usual means known in the art.

In the prior art process chromatographic separation is quite often required at this point or in the next step to purify the product. In the instant invention in step "F" the crude reaction product (2) is treated with a benzyl halide, preferably bromide or chloride, in an aprotic solvent, such as N,N-dimethylformamide, with an alkali carbonate such as potassium carbonate. The mixture is allowed to react at 15°-25° C. in an inert atmosphere, such as nitrogen or argon, until the reaction is complete as monitored by thin layer chromatography. Additional benzyl halide and an alkali carbonate are added at intervals during the reaction time. The product is then isolated according to known methods.

In the instant invention in step "G" the reaction product from step "F" is treated with, for example, propanediamine at elevated temperatures, for example, 75°-110° C., for approximately eight to eighteen hours or at 110°-130° C. for approximately one to seven hours. The product is then isolated by known methods.

In step "H" of the instant invention the reaction product from step "H" is dissolved in an alcohol solvent, such as methanol, and glacial acetic acid and hydrogenated using a palladium on carbon catalyst at 15°-25° C. and 15°-50 psi.

The product of the reaction is isolated and purified by standard procedures.

By further way of illustration, step "J" is carried out by treating the reaction product from step "F" with, for example, N-methyl-N-phenyl-methyl-1,2-ethanediamine neat or in a solution of N-methyl-2-pyrrolidinone with an alkali fluoride catalyst, such as potassium fluoride.

The reaction is allowed to proceed for from 4–12 hours at elevated temperature for example, at 130°-150° C. The product is isolated by known means.

In step "K" of the instant invention the reaction product from step "J" is dissolved in an alcohol solvent such as methanol together with glacial acetic acid. The reaction product from step "J" is hydrogenated over a palladium on carbon catalyst at 15°-25° C. at atmospheric pressure or under slight pressure. The products of the reaction are isolated and purified by standard procedures.

The process of the prior art is described in examples 1–6.

The process of this invention is described by the following nonlimiting examples, numbers 1 and 7–14. These are presented to exemplify the invention and are not to be construed as limiting the invention's scope.

EXAMPLE 1

5-Chloro-2-[2-[(2-hydroxyethyl)amino]ethyl-7,10-bis (phenylmethoxy)-anthra[1,9-cd]pyrazol-6(2H)-one (2)

A mixture of 300 g (0.613 mol) of 1,4-dichloro-5,8-bis(phenylmethoxy)-9,10-anthracenedione (1), 219 g (1.84 mol) of 2-[(hydrazinoethyl)amino]ethanol, 18 g (0.31 mol) of potassium fluoride and 60 g (0.60 mol) of dried potassium bicarbonate in 1 l of dimethylacetamide (predried over 4A molecular sieves), was stirred and heated at 69° C. under nitrogen for 18 hours. The reaction mixture was allowed to cool to room temperature, diluted with 3.5 l of methanol, 600 ml of water, and finally 500 ml of ethanol. After drying there were obtained 223 g of crude 2 (66% of theory).

A 165 g sample of this material was chromatographed on a 3 kg column of silica gel (230–400 mesh), eluting with chloroform and then chloroform-methanol. Some of the product fractions were combined, freed from solvent under vacuum, slurried in ethyl ether, and filtered to give, after drying, 84.6 g of 2, mp 178.5–180.5, 99.5% pure by HPLC. Chromatographic yield 51%, overall 34%.

EXAMPLE 2

5-[(3-Aminopropyl)amino]-2-[2-[(2-hydroxyethyl)amino]ethyl]-7,10-bis-(phenylmethoxy)anthra[1,9-cd]pyrazol6(2$\underline{H}$)-one (3)

A mixture of 84.6 g (0.15 mol) of 5-chloro-2-[2-[(2-hydroxyethyl)amino]ethyl]-7,10-bis(phenylmethoxyanthra[1,9-cd]pyrazol-6(2$\underline{H}$)-one (2) which had been purified by chromatography and 202 g (2.73 mol) of 1,3-propanediamine was stirred under nitrogen for 2.5 hours at 90° C. Initially, 2 dissolved in the hot reaction mixture but then a pasty precipitate formed which was difficult to stir. Another 133 g (1.80 mol) of 1,3-propanediamine was added, and the temperature was raised to 115° C. where solution was nearly complete. After stirring at 115° C. for an additional three hours, the reaction mixture was allowed to cool to room temperature overnight, stirred into a mixture of 750 ml of water and 750 ml of 2-propanol, filtered, washed with 2 l of a similar mixture, 2 l of water and then 8 l of methanol. After drying there were obtained 73 g (86% of theory) of (3) which was about 96.3 % pure by HPLC.

EXAMPLE 3

5-[(3-Aminopropyl)amino]-2-[2-(2-hydroxyethyl)amino]ethyl]-7,10-bis(phenylmethoxy)anthra[1,9-cd]pyrazol-6(2$\underline{H}$)-one (3)

Under a slow stream of argon gas, a mixture of 19.4 g (0.035 mol) of crude 5-chloro-2-[2-[(2-hydroxyethyl)amino]ethyl]-7,10-bis(phenylmethoxy)anthra[1,9-cd]-pyrazol-6(2$\underline{H}$)-one (2) and 29 ml (25.8 g, 0.35 mol) of 1,3-propanediamine was stirred at 130° C. for 3.5 hours, allowed to cool and triturated with water and 2-propanol. The solid was collected, washed successively with water, 2-propanol and ethanol, and dried under vacuum at 40° C. to give 16.9 g of crude product. Chromatography over 1 kg of silica gel (230–400 mesh) with a mixture of methanol:dichloromethane:triethylamine in the following ratios: 20:79:1, then 30:69:1, and finally 40:59:1 provided 11 g. This material was recrystallized from pyridine, washed with 2-propanol, and dried under vacuum overnight at 60° C. to afford 9.7 g (46.8%) of 3, mp 204°–206° C.

EXAMPLE 4

5-[(3-Aminopropyl)amino]-7,10-dihydroxy-2-[2-[(2-hydroxyethyl)amino]ethyl]anthra[1,9-cd]pyrazol-6(2$\underline{H}$)-one, hydrochloride (5:9) (4)

A mixture of 9.5 g (0.016 mol) of 5-[(3-aminopropyl)amino]-2-[2-(2-hydroxyethyl)amino]ethyl]-7,10-bis(-phenylmethoxy)anthra[1,9-cd[pyrazol-6(2$\underline{H}$)-one (3) in 300 ml of acetic acid was hydrogenated over 1.7 g of 20% palladium hydroxide on carbon at atmospheric pressure and at room temperature for two hours, filtered through celite, and concentrated under vacuum. The residue was dissolved in boiling methanol. The hot solution was treated with an excess (about 0.05 mol) of hydrogen chloride in 2-propanol, and chilled overnight. The red-orange precipitate was collected, washed with 2-propanol, dried at 65° C. under vacuum for 48 hours, and allowed to equilibrate in the air overnight to afford 6.4 g (82%) of 4, containing 0.6 mole of water, mp 267°–272° C. (dec) with prior sintering.

Overall yield via steps A, B, C=24–25%.

EXAMPLE 5

2-[2-[(2-Hydroxyethyl)amino]ethyl]-5-[[2-[methyl(-phenylmethyl)amino]amino]-7,10-bis (phenylmethoxy)-anthra[1,9-cd]pyrazol-6-(6-(2$\underline{H}$)one (5)

Under a slow stream of argon, a mixture of 100.3 g (0.175) of crude 5-chloro-2-[2-(2-hydroxyethyl)-7,10-bis(phenylmethoxy)anthra[1,9-cd]pyrazol-6(2/ )one (2), 264 g (1.6 mol) of N-methyl-N-(phenylmethyl)-1,2-ethanediamine, 3 g (0.05 mol) of dried potassium fluoride and 25 ml of N-methylpyrrolidione was dried in a 132° C. oil bath for four hours, allowed to cool to 90° C., diluted with 800 ml of aqueous 2-propanol, and allowed to stand with occasional stirring. The precipitate was collected, washed successively with water, ethanol and ether, and dried to afford 76.9 g of crude 5. Chromatography over 2600 g of silica gel (230–400 mesh) using a gradient elution of 5–15% methanol in dichloromethane followed by trituration with methanol and finally recrystallization from toluene:pyridine (1:1) afforded material which was clean by TLC (SiO$_2$-methanol:dichloromethane triethylamine, 20:80:1), R$_f$=0.38. This material was ground to a powder and dried under vacuum at 80° C. for 18 hours to afford 38.8 g (32.1%) of 5, mp 144°–146° C.

EXAMPLE 6

7,10-Dihydroxy-2-[[(2-hydroxyethyl)amino[ethyl[-5-[[(2-methylamino)ethyl]amino]anthra[1,9-cd]pyrazol-6(2$\underline{H}$)one, hydrobromide (20:39) (6)

A mixture of 38.8 g (0.057 mol) of 2-[2-[(2-hydroxyethyl)amino)ethyl]-5-[[2-[methyl(phenylmethyl)-amino[ethyl]amino-7,10-bis(phenylmethoxy)anthra[1,9-cd]pyrazol-6(2$\underline{H}$)one (5) in 850 ml of glacial acetic acid was hydrogenated over 20% palladium on carbon at room temperature and at 20 psi six hours and then filtered through supercell. The filtrate was treated with 14 ml of 48% hydrobromic acid in 200 ml of 2-propanol, chilled overnight and filtered. The precipitate was washed with a little acetic acid, then with ethanol, and finally with ether and dried to afford 28 g of crude 6. This material was taken up in 650 ml of boiling N,N-dimethylformamide and the mixture was filtered hot to collect about 3 g of undissolved product which was washed with 2-propanol and ether. The filtrate was cooled and treated with 1 l of 2-propanol and 4 ml of 48% hydrobromic acid. The resulting precipitate was collected, washed with 2-propanol and ether. The two crops were combined, dried under vacuum at 75°–85° C., and allowed to equilibrate in air to afford 24 g (71%) of 6, mp 270°–273° C. (dec) as a red orange solid. Overall yield via steps A, D, E=15%.

EXAMPLE 7

5-Chloro-2-[2-[(2-hydroxyethyl)(phenylmethyl)amino-ethyl]-7,10-bis(phenylmethoxy)anthra[1,9-cd[pyrazol-6(2$\underline{H}$)-one (7)

Under an atmosphere of argon gas, a mixture of 620 g (1.12 mol) of crude 5-chloro-2-[2-[2-hydroxyethyl)amino]ethyl]-7,10-bis(phenylmethoxy)anthra[1,9-cd]pyrazol-6(2$\underline{H}$)-one (2), 75 ml of α-bromotoluene and 75 g of anhydrous potassium carbonate in 3 l of N,N- dimethylformamide was stirred at room temperature for 117 hours. An additional 10 ml of α-bromotoluene and 10 g of potassium carbonate were added after 21 hours of stirring and again after 48 hours of stirring; 80 ml of α-bromotoluene and 30 g of potassium carbonate were added after 52 hours. The precipitate was collected, washed first with acetonitrile, then with water, and again with acetonitrile, and dried under vacuum (0.3 torr) at 90° C. for three hours and then at 70° C. for 16 hours to afford 488 g (67.7%) of 7, mp 178°–181° C., 95.3% pure by HPLC.

EXAMPLE 8

5-[(3-Aminopropyl)amino]-2-[2-[(2-hydroxyethyl)(-phenylmethyl)amino]ethyl]-7,10-bis (phenylmethoxy)anthra]1,9-cd[pyrazol-6(2H)-one (8)

Under an atmosphere of argon gas, a mixture of 74.2 g (0.115 mol) of 5-chloro-2-[2-[(2-hydroxyethyl)(-phenylmethyl)amino]ethyl]-7,10-bis(phenylmethoxy)anthra[1,9-cd]pyrazol-6(2H)-one (7) and 150 g of 1,3-propanediamine was stirred at 75°–80° C. for 18 hours and at 110° C. for one hour, allowed to cool, and triturated with dichloromethane.

The resulting precipitate was collected and washed with additional dichloromethane, then with methanol, dilute sodium bicarbonate solution and water, again with methanol, and finally with dichloromethane. The air dried solid was then dried under vacuum (0.1 torr) at 80° C. to afford 42 g (53.5%) of 8, mp 192°–196° C. and 99% pure by HPLC.

EXAMPLE 9

5-[(3-Aminorpopyl)amino]-2-[2-[(2-hydroxyethyl)(-phenylmethyl)amino]ethyl]-7,10-bis (phenylmethoxy)anthra[1,9-cd[pyrazol-6(2H)-one (8)

Under an atmosphere of argon gas, a mixture of 5 g (0.0078 mol) of 5-chloro-2-[2-[(2-hydroxyethyl)(phenylmethyl)amino]ethyl]-7,10-bis(phenylmethoxy)anthra[1,9-cd[pyrazol-6(2H)-one (7) and 15.8 g (0.21 mol) of 1,3-propanediamine was stirred at 110° C. for 3.5 hours, allowed to cool to 80° C., and poured into aqueous methanol. The precipitate was collected and washed with ethanol and methanol, suspended in hot methanol, and again collected to afford 3.5 g (66%) of 8, mp 190°–192° C.

EXAMPLE 10

5-[(3-Aminopropyl)amino]-7,10-dihydroxy-2-[2-[(2-hydroxyethyl)amino]ethyl]anthra[1,9-cd]pyrazol-6(2H)-one (4)

A solution of 41.1 g (0.06 mole) of 5-[(3-aminopropyl)amino]-2-[2-[(2-hydroxyethyl) (phenylmethyl)-amino]ethyl]-7,10-bis(phenylmethoxy)anthra]1,9-cd]pyrazol-6(2H)one (8) in 700 ml of methanol and 100 ml of glacial acetic acid was hydrogenated over 1 g of 20% palladium on carbon at room temperature and at an initial pressure of 15 pounds for 8.6 hours. The mixture was filtered through celite and concentrated under vacuum to dryness. The residual oil was dissolved in 1500 ml o hot methanol and treated with excess of a solution of hydrogen chloride in 2-propanol. The precipitate which formed was collected, washed with methanol, and dried under vacuum (200 torr) at 75° C. for 24 hours and allowed to equilibrate in air to afford 27.4 g (90.6%) of 3, mp 295°–300° C. (dec) which analyzes for .2HCl.0.9H$_2$O and is 99.6% pure by HPLC.

Overall yield via step A (without chromatography) F, G, H=27%.

EXAMPLE 11

2-[2-[(2-Hydroxyethyl)(phenylmethyl)amino]ethyl]-5-[[2-[methyl(phenylmethyl)amino]ethyl]amino]-7,10-bis(phenylmethoxy)anthra[1,9-cd]pyrazol]-6(2H)-one (9)

In an atmosphere of nitrogen, a mixture of 179 g (0.278 mol) of 5-chloro-2-[2-[(2-hydroxyethyl)(phenylmethyl)amino]ethyl]-7,10-bis(phenylmethyl)anthra-[1,9-cd]pyrazol-6(2H)-one (7) and 400 ml (2.43 mol) of N-methyl-N-phenylmethyl-1,2-ethanediamine [M. Freifelder, *J. Am. Chem. Soc.*, 82, 2386 (1960)] was heated to 160° C. over a 15-minute period and maintained at 155°–160° C. for one hour. The resulting red solution was allowed to cool to 100° C. and poured into 2-propanol. The resulting thick red slurry was filtered and pressed under a rubber dam overnight. The filter cake was then suspended in water, stirred vigorously for two hours, filtered, and dried under a slight vacuum at 80° C. for 24 hours to give 159.4 g of an orange solid. This material was then stirred for two hours in hot ethyl acetate (2.5 l) refrigerated overnight, filtered, washed with ether (2 l) and dried under vacuum to give 129.7 g (60%) of 9, mp 147°–149° C.

EXAMPLE 12

7,10-Dihydroxy-2-[2-[(2-hydroxyethyl)amino]ethyl]-5-[[2-(methylamino)ethyl]amino]anthra[1,9-cd]pyrazol-6(2H)one, hydrochloride (10:19) (6)

A mixture of 11.6 g (0.015 mol) of 2-[2-[(2-hydroxyethyl)(phenylmethyl)amino]ethyl]-5-[[2-[methyl(phenylmethyl)amino]ethyl]amino]-7,10-bis (phenylmethoxy)anthra[1,9-cd]pyrazol-6(2H)one (9), 120 ml of methanol, and 40 ml of glacial acetic acid was hydrogenated over 1 g of 20% palladium on carbon at room temperature and at an initial pressure of 15 psi for 48 minutes, filtered, and then concentrated under vacuum. The residual oil was dissolved in 300 ml methanol and the solution was treated with charcoal and filtered through celite, and then treated with 6 ml of 26% hydrogen chloride in 2-propanol. The resulting precipitate was collected, washed with methanol, 2-propanol, and ether, dried at 200 torr at 100° C. for three hours to afford 6.1 g (83.9) of 6.

Overall yield via steps A, F, J, K=22.6%.

We claim:

1. A process for the preparation of a substituted anthra[1,9-cd]pyrazol-6(2H)-one having the formula

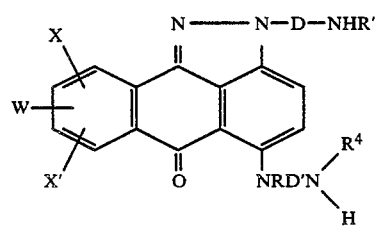

wherein X, X', and W may be the same or different and are H or OH; R is H or alkyl of from one to six carbon atoms; D and D' may be the same or different and are a straight or branched alkylene group of from two to eight carbon atoms, R$_4$ is H or an alkyl group of one to eight carbon atoms, and R' is an alkyl group of from two to eight atoms which may be substituted with OH which comprises:

(a) reacting a compound having the formula

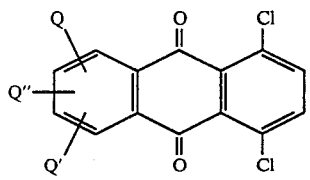

with a hydrazine of formula H$_2$NNHDNHR', wherein Q, Q', and Q" may be the same or different and are H, benzyloxy, p-chlorobenzyloxy and p-methoxybenzyloxy, and D and R' are as defined above, to give a compound of formula

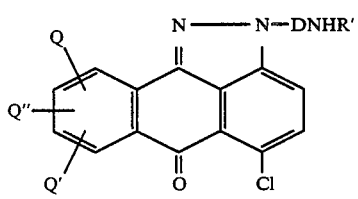

(b) reacting a compound of structural Formula VII with a benzyl halide in a suitable solvent and in the presence of an alkali carbonate to give a compound of formula

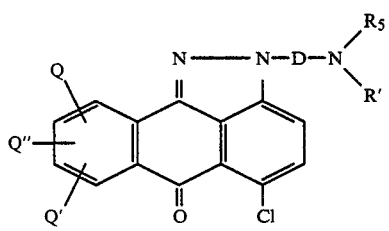

wherein Q, Q', Q", D, and R' are defined above and R$_5$ is benzyl;

(c) reacting a compound of Formula VIII with a diamine of the formula

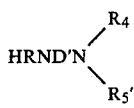

in which R$_5$' is H or benzyl in a suitable solvent to produce a compound of formula

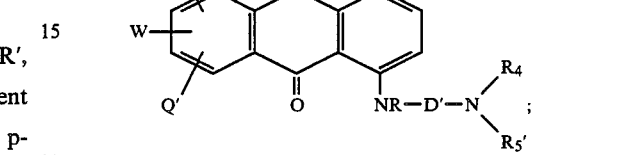

(d) removing the benzyl groups by catalytic means.

2. The process of claim 1, wherein in step (b) benzyl bromide is used.

3. The process of claim 1, wherein in step (b) the solvent is in N,N-dimethylformamide.

4. The process of claim 3, wherein in step (b) the alkali carbonate is potassium carbonate.

5. The process of claim 1, wherein in step (b) the reaction is carried out at room temperature until the reaction is complete.

6. The process of claim 1, wherein in step (c) a diamine of the formula H$_2$ND'NH$_2$, wherein D' is an alkylene of from two to eight carbon atoms is used.

7. The process of claim 6, wherein in step (c) the diamine used is 1,3 propanediamine.

8. The process of claim 1, wherein in step (c) a diamine of the formula

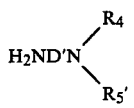

wherein D' is an alkylene group of from two to eight carbon atoms, R$_4$ is H or an alkyl group of from one to eight carbon atoms, R$_5$' is benzyl.

9. The process of claim 8, wherein in step (c) the diamine is N-methyl-N-phenylmethyl-1,2-ethanediamine.

10. The process of claim 1, wherein in step (c) the solvent is N-methyl-2-pyrrolidinone and the reaction is carried out in the presence of potassium fluoride.

11. The process of claim 1, wherein in step (c) the reaction proceeds from one to seven hours at temperature between 110° C. and 130° C.

* * * * *